(12) United States Patent
Sa et al.

(10) Patent No.: US 9,827,561 B2
(45) Date of Patent: Nov. 28, 2017

(54) LIGAND COMPOUND, CATALYST SYSTEM FOR OLEFIN OLIGOMERIZATION, AND OLEFIN OLIGOMERIZATION METHOD USING THE SAME

(71) Applicant: LG CHEM, LTD., Seoul (KR)

(72) Inventors: Seok Pil Sa, Daejeon (KR); Yong Ho Lee, Daejeon (KR); Ki Soo Lee, Daejeon (KR); Eun Ji Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/032,008

(22) PCT Filed: Nov. 17, 2014

(86) PCT No.: PCT/KR2014/011029
§ 371 (c)(1),
(2) Date: Apr. 25, 2016

(87) PCT Pub. No.: WO2015/072799
PCT Pub. Date: May 21, 2015

(65) Prior Publication Data
US 2016/0271600 A1   Sep. 22, 2016

(30) Foreign Application Priority Data

Nov. 18, 2013 (KR) .................. 10-2013-0139996
Nov. 14, 2014 (KR) .................. 10-2014-0158962

(51) Int. Cl.

| | |
|---|---|
| *B01J 31/24* | (2006.01) |
| *C07F 9/46* | (2006.01) |
| *C07F 9/572* | (2006.01) |
| *C07F 9/58* | (2006.01) |
| *C07F 9/6506* | (2006.01) |
| *C07F 9/6509* | (2006.01) |
| *C07F 9/655* | (2006.01) |
| *C07F 9/6553* | (2006.01) |
| *C08F 4/42* | (2006.01) |
| *B01J 31/14* | (2006.01) |
| *C07C 2/32* | (2006.01) |
| *C07F 9/28* | (2006.01) |
| *C08F 110/02* | (2006.01) |

(52) U.S. Cl.
CPC ......... *B01J 31/2409* (2013.01); *B01J 31/143* (2013.01); *C07C 2/32* (2013.01); *C07F 9/28* (2013.01); *C07F 9/46* (2013.01); *C07F 9/5721* (2013.01); *C07F 9/5727* (2013.01); *C07F 9/588* (2013.01); *C07F 9/65061* (2013.01); *C07F 9/65067* (2013.01); *C07F 9/65515* (2013.01); *C07F 9/650958* (2013.01); *C07F 9/650988* (2013.01); *C07F 9/655345* (2013.01); *C08F 4/42* (2013.01); *C08F 110/02* (2013.01); *B01J 2231/20* (2013.01); *B01J 2531/002* (2013.01); *B01J 2531/62* (2013.01); *C07C 2531/12* (2013.01); *C07C 2531/22* (2013.01)

(58) Field of Classification Search
CPC .............. B01J 2231/20; B01J 2531/002; B01J 2531/62; B01J 31/143; B01J 31/2409; C07C 2531/12; C07C 2531/22; C07F 9/28; C07F 9/46; C07F 9/5721; C07F 9/5727; C07F 9/588; C07F 9/65061; C07F 9/65067; C07F 9/650958; C07F 9/650988; C07F 9/65515; C07F 9/655345; C08F 110/02; C08F 4/42
See application file for complete search history.

(56) References Cited

U.S. PATENT DOCUMENTS

| | | | |
|---|---|---|---|
| 8,076,523 | B2 | 12/2011 | Bollmann et al. |
| 2015/0329440 | A1 | 11/2015 | Shin et al. |

FOREIGN PATENT DOCUMENTS

| | | |
|---|---|---|
| CN | 1651142 A | 8/2005 |
| CN | 103044181 A | 4/2013 |
| CN | 104884165 A | 9/2015 |
| EP | 2899196 A1 | 7/2015 |
| JP | 2006-511694 A | 4/2006 |
| JP | 2006-517528 A | 7/2006 |
| KR | 1020120138309 A | 12/2012 |
| WO | 2002/065526 A1 | 8/2002 |
| WO | 2008004986 A1 | 1/2008 |

OTHER PUBLICATIONS

Fei, et al., Transformation between Diphosphinoamines and Iminobiphosphines, Inorg. Chem., vol. 43, 2228-2230 (2004).*
By Song, et al, Syntheses, Structures, and Catalytic Ethylene Oligomerization Behaviors of Bis(phosphanyl)aminenickel(II) Complexes Containing N-Functionalized Pendant Groups, Eur. J. Inorg. Chem., 3016-3024 (2009).*
Weng, et al, Chromium (III) catalyzed ethylene tetramerization promoted by bis(phosphino)amines with an N-functionalized pendant, Dalton Trans., 3493-3498 (2007).*

(Continued)

*Primary Examiner* — Erich A Leeser
(74) *Attorney, Agent, or Firm* — Dentons US LLP

(57) ABSTRACT

The present invention relates to a ligand compound, a catalyst system for olefin oligomerization, and a method for olefin oligomerization using the same. The present ligand compound is a compound having a certain new structure and enables provision of a catalyst system for olefin oligomerization that can oligomerize ethylene with higher catalytic activity.

13 Claims, No Drawings

(56) References Cited

OTHER PUBLICATIONS

Matthew J. Overett, et al., "Ethylene trimerisation and tetramerisation catalysts with polar-substituted diphosphinoamine ligands", Chem. Commun., 2005, 622-624.

Anthea Carter, et al., "High activity ethylene trimerisation catalysts based on diphosphine ligands", Chem. Commun., 2002, 858-859.

Kevin Blann, et al., "Ethylene tetramerisation: Subtle effects exhibited by N-substituted diphosphinoamine ligands", Journal of Catalysis, 249 (2007) 244-249.

Keming Song, et al., "Syntheses, Structures, and Catalytic Ethylene Oligomerization Behaviors of Bis(phosphanyl)aminenickel(II) Complexes Containing N-Functionalized Pendant Groups", Eur. J. Inorg. Chem. 2009, pp. 3016-3024.

Zhiqiang Weng, et al., "Chromium(III) catalysed ethylene tetramerization promoted by bis(phosphino)amines with an N-functionalized pendant," Dalton Trans., 2007, No. 32, pp. 3493-3498.

Zhaofu Fei, et al. "Transformation between Diphosphinoamines and Iminobiphoshines: a Reversable P-N-PP-N=P-P Rearrangement Triggered by Protonation/Deprotonation", Inorg. Chem, 2004, vol. 43, pp. 2228-2230.

Kevin Blann, et al., "Highly Selective Chromium-based ethylene trimerisation catalysts with bulky diphosphinoamine ligands," Chem. Commun., 2005, 620-621.

Alzamly, et al.: "Reactivity with Alkylaluminium of a Chromium Complex of a Pyridine-Containing PNP Ligand: Redox N-P Bond Cleavage", Organometallics, vol. 33, Mar. 18, 2014, pp. 1602-1607.

Zhang, et al.: "Synthesis of Diphenylphosphinoamine Ligands and Their Catalytic Performance for Ethylene Tetramerization with Cr(III) Compounds", Chinese Journal of Catalysis, vol. 27, No. 5, May 2006, pp 416-420.

Zhang, et al.: "Synthesis and coordination chemistry of aminophosphine derivatives of adenine", Dalton Transactions, The Royal Society of Chemistry, Jul. 7, 2003, pp. 3250-3257.

Robert, et al.: "Crystal structure of (S)-1-[bis(diphenylphosphino)amino]-2-(methoxy-methyl)pyrrolidine, C30H32N2OP2", Kristallographie, New Crystal Structures, vol. 214, May 20, 1999, pp. 581-582.

Belyaev: "Effect of oral administration of some chelating agents on the excretion of plutonium in rats", Raspredelenie, Biol. Deistvie, Uskorenie Vyvedeniya Radioaktivn. Izotopov, 1964, pp. 338-342.

Zhaofu, et al.: "Phosphorylation of Diaminopyridines: Synthesis of a Compound Containing Both a Diphosphinoamine (P-N-P) and an Iminobiphoshine (N=P-P) Fragment", European Journal of Inorganic Chemistry, 2014, pp. 1745-1750.

Ok, F., et al., "Novel half-sandwich n5-Cp *-rhodium(III) and n5-Cr*ruthenium(II) complexes bearing bis(phosphino)amine ligands and their use in the transfer hydrogenation of aromatic ketones," Applied Organometric Chemistry, 28(1), 2014, pp. 38-43, XP-002767425.

Wang Y., et al., "Synthesis and characterisation of three diiron tetracarbonyl complexes related to the diiron centre of [FeFe]-hydrogenase and their protonating, electrochemical investigations," New J. Chem, 33(8), 2009, pp. 1780-1789, XP-002767426.

* cited by examiner

LIGAND COMPOUND, CATALYST SYSTEM FOR OLEFIN OLIGOMERIZATION, AND OLEFIN OLIGOMERIZATION METHOD USING THE SAME

This application is a National Stage Application of International Application No. PCT/KR2014/011029, filed Nov. 17, 2014, and claims the benefit of Korean Patent Application No. 10-2014-0158962, filed Nov. 14, 2014 and Korean Patent Application No. 10-2013-0139996, filed Nov. 18, 2013, the contents of which are incorporated herein by reference in their entirety for all purposes as if fully set forth below.

TECHNICAL FIELD

The present invention relates to a ligand compound, a catalyst system for olefin oligomerization, and a method for olefin oligomerization using the same.

BACKGROUND

A linear alpha-olefin, which is an important material used for a comonomer, a cleaning agent, a lubricant, a plasticizer, and the like, is commercially widely used, and particularly, 1-hexene and 1-octene are frequently used as a comonomer for controlling the density of polyethylene when preparing a linear low-density polyethylene (LLDPE) and the like.

More specifically, in the existing preparation process of LLDPE (linear low-density polyethylene), ethylene is copolymerized with alpha-olefin comonomers such as 1-hexene and 1-octene, so as to form a branch in a polymer backbone to control the density thereof.

Thus, there is a problem in that the cost of comonomers accounts for a large part of the production cost in the preparation of LLPDE having a high comonomer content. Accordingly, various attempts have been made to reduce the production cost of the comonomers.

Also, since alpha-olefins have a different application field or market size according to the kind, a technology for selectively producing specific alpha-olefins is commercially very important, and recently, many studies have been carried out on a chromium catalyst technology for preparing 1-hexene or 1-octene with high selectivity through selective ethylene oligomerization.

The existing commercial methods for preparing 1-hexene or 1-octene include a SHOP process of Shell Chemicals, a Ziegler process of Chevron Philips, and the like, whereby $C_4$-$C_{20}$ alpha-olefins with wide distributions can be produced.

As a catalyst used in the production of selective alpha-olefins, for example, as an existing catalyst for trimerization of ethylene, a chromium-based catalyst using a ligand of a General Formula (R1)(R2)X—Y—X(R3)(R4) has been suggested. In the Formula, X is phosphorous, arsenic, or antimony, Y is a linking group such as —N(R5)-, and at least one of R1, R2, R3, and R4 has a polar or electron donating substituent.

In addition, as a ligand that does not exhibit catalytic activity to 1-hexene under a catalytic condition, studies have been carried out on (o-ethylphenyl)$_2$PN(Me)P(o-ethylphenyl)$_2$, a compound which does not have a polar substituent on at least one of R1, R2, R3, and R4 (*Chem. Commun.*, 2002, 858).

However, the existing ligand containing a heteroatom as described above, and the chromium-based catalyst obtained therefrom, are difficult to consistently and excellently exhibit multimerization activity, for example, during the production of 1-octene or 1-hexene, and the selectivity thereof is also not sufficient. Thus, there is continued demand for improving them.

Technical Problem

The present invention provides a new ligand compound that can selectively oligomerize ethylene while exhibiting high catalytic activity, a catalyst system for olefin oligomerization comprising the same, and a method for olefin oligomerization using the same.

Technical Solution

The ligand compound according to an aspect of the present invention may be represented by the following Chemical Formula 1:

[Chemical Formula 1]

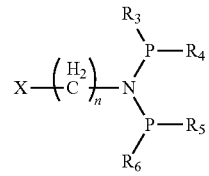

in Chemical Formula 1,
X is —$NR_1R_2$, or a substituted or unsubstituted heterocyclic functional group containing one or more heteroatoms of N, O or S,
$R_1$ and $R_2$ are each independently a $C_1$-$C_{20}$ alkyl group containing one or more heteroatoms of N, O, F, S or P, a $C_3$-$C_{20}$ cycloalkyl group, a $C_6$-$C_{40}$ aryl group, a $C_3$-$C_{30}$ heteroaryl group, —$PR_3R_4$ or a $C_7$-$C_{40}$ arylalkyl group,
$R_3$ to $R_6$ are each independently a $C_1$-$C_{40}$ hydrocarbon group optionally containing one or more heteroatoms of N, O, F, S or P, and
n is an integer of 0 to 10.

The catalyst system for olefin oligomerization according to another aspect of the present invention may comprise a ligand compound represented by Chemical Formula 1; a transition metal source; and a cocatalyst.

The method for olefin oligomerization according to yet another aspect of the present invention may comprise the step of multimerizing olefins in the presence of the catalyst system for olefin oligomerization comprising the ligand compound represented by Chemical Formula 1, a transition metal source and a cocatalyst.

Advantageous Effects

By using a catalyst system comprising the ligand compound according to the present invention, ethylene can be oligomerized with higher catalytic activity as compared with the existing catalyst system.

DETAILED DESCRIPTION OF THE EMBODIMENTS

A variety of modifications may be made to the present invention, and the present invention may be embodied in many different forms, particular embodiments of which will be now provided and described in detail. However, these are not intended to limit the present invention to certain embodiments, and it shall be appreciated that all modifications, equivalents or substitutes covered by the technical ideas and scopes of the present invention are included in the description. In describing the present invention, when certain detailed description of relevant known art is considered to make the gist of the present invention unclear, such detailed description will be omitted.

The present invention provides a ligand compound represented by the following Chemical Formula 1:

[Chemical Formula 1]

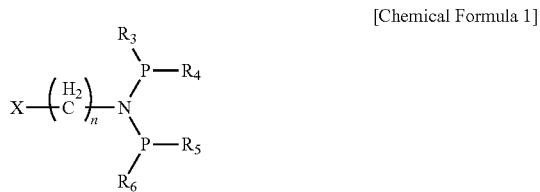

in Chemical Formula 1,

X is $-NR_1R_2$, or a substituted or unsubstituted heterocyclic functional group containing one or more heteroatoms of N, O or S, $R_1$ and $R_2$ are each independently a $C_1$-$C_{20}$ alkyl group containing one or more heteroatoms of N, O, F, S or P, a $C_3$-$C_{20}$ cycloalkyl group, a $C_6$-$C_{40}$ aryl group, a $C_3$-$C_{30}$ heteroaryl group, $-PR_3R_4$ or a $C_7$-$C_{40}$ arylalkyl group, $R_3$ to $R_6$ are each independently a $C_1$-$C_{40}$ hydrocarbon group optionally containing one or more heteroatoms of N, O, F, S or P, and n is an integer of 0 to 10.

Also, in accordance with another aspect of the present invention, there is provided a catalyst system for olefin oligomerization comprising the ligand compound represented by Chemical Formula 1; a chromium source; and a cocatalyst.

In addition, in accordance with yet another aspect of the present invention, there is provided a method for olefin oligomerization comprising: the step of multimerizing olefins in the presence of the catalyst system for olefin oligomerization comprising the ligand compound represented by Chemical Formula 1, a chromium source and a cocatalyst.

As already mentioned above, a conventional catalyst system for olefin oligomerization has a disadvantage that it is difficult to exhibit consistent and excellent multimerization activities. Thus, the present inventors have continuously conducted studies to improve these disadvantages, synthesized a ligand compound having a novel structure of Chemical Formula 1, and found that it is possible to provide a catalyst system for oligomerization having excellent multimerization activities by using the above ligand compound, thereby completing the present invention. In particular, it has been found that the catalyst system for oligomerization provided using a ligand compound of Chemical Formula 1 can consistently exhibits excellent multimerization activities during oligomerization of olefin, for example, ethylene, as supported by Examples that will be described later. It is predicted that the excellent activity of the catalyst system for oligomerization is expressed due to $-NR_1R_2$ (especially, certain types of $R_1$, $R_2$) or heterocyclic functional group that is bonded to the position of X. On the other hand, when the structure of the functional group bonded to the position of X is a little different (for example, when $R_1$ and $R_2$ are hydrogen or a $C_1$-$C_3$ alkyl group such as a methyl group, etc.), it was confirmed that the aforementioned superior activity cannot be expressed.

Ultimately, according to the present invention, the catalyst system for oligomerization having consistent and excellent activities as compared with a conventional catalyst system, and a novel ligand compound enabling provision of such catalyst system can be provided.

Hereinafter, the ligand compound of the present invention, the catalyst system for olefin oligomerization, and the method for olefin oligomerization using the same will be described in more detail.

The ligand compound of the present invention can be represented by Chemical Formula 1:

[Chemical Formula 1]

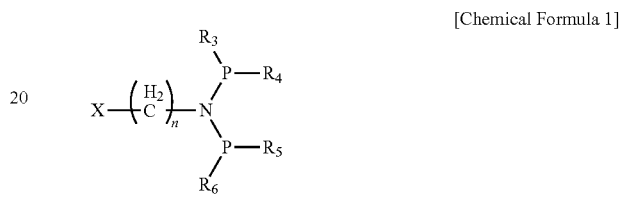

in Chemical Formula 1, X, $R_3$ to $R_6$, and n are as defined above.

In particular, considering the aspect of excellent activity of the catalyst system for oligomerization provided by the aforementioned ligand compound, in Chemical Formula 1, X may be $-NR_1R_2$, a $C_3$-$C_8$ heterocyclic functional group having N in the ring substituted or unsubstituted with $C_1$-$C_3$ alkyl group, or an unsubstituted $C_3$-$C_8$ heterocyclic functional group having O or S in the ring, $R_1$ and $R_2$ may be each independently a $C_3$-$C_{20}$ cycloalkyl group or $-PR_3R_4$, $R_3$ to $R_6$ may be each independently a $C_6$-$C_{40}$ aryl group, and n may be an integer of 1 to 5.

In a more specific embodiment, the X may be $-NR_1R_2$ (provided that $R_1$ and $R_2$ are each independently a cyclohexyl group, a cyclopentyl group or $-PR_3R_4$), or

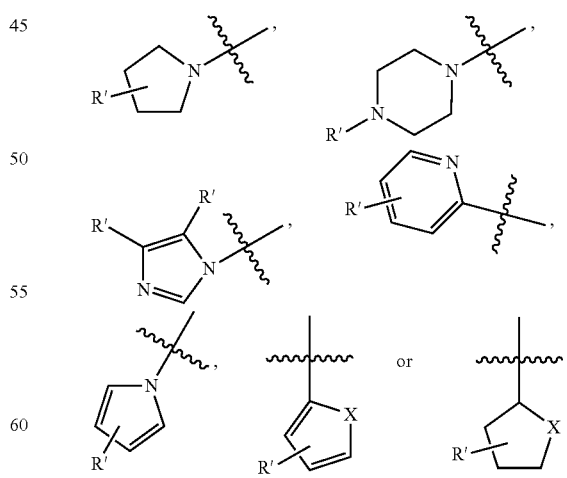

(provided that R' is hydrogen or $C_1$-$C_3$ alkyl group, and X is O or S), $R_3$ to $R_6$ may be a phenyl group, and n may be an integer of 1 to 5.

In addition, according to the most specific embodiment, the ligand compounds represented by Chemical Formula 1 may be selected from the group consisting of the following compounds, however, the ligand compounds of the present invention are not limited thereto and these are presented as an illustrative example.

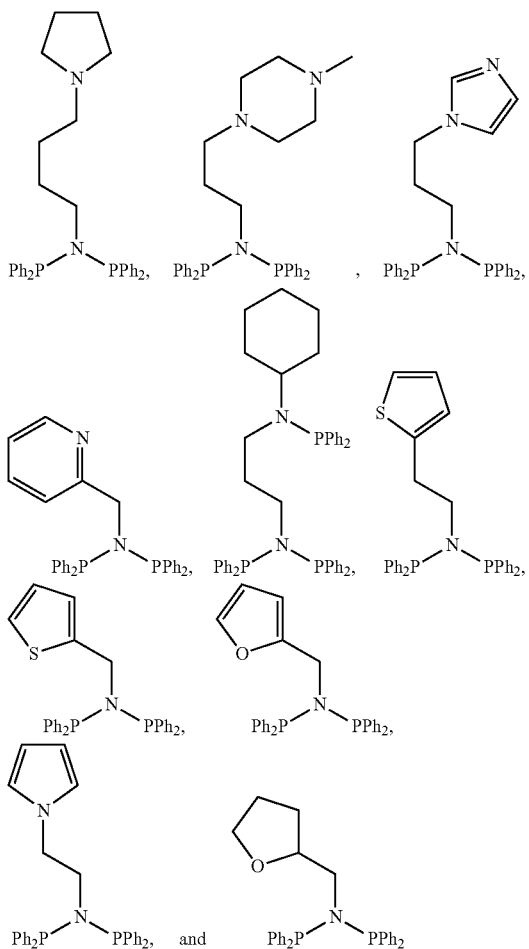

The ligand compounds of Chemical Formula 1 can be prepared according to the reaction condition and method commonly applied for the preparation of the ligand compounds having two or more structures of —PR"R'" (R" and R'" are each independently a hydrocarbon group such as an aryl group), and the specific reaction conditions and methods thereof are also described in Examples below.

For example, the ligand compounds of Chemical Formula 1 can be prepared by reacting an amine compound having a structure of X—(CH$_2$)—NH$_2$ and a compound having a structure of Cl—PR"R'" (where R" and R'" are each independently a hydrocarbon group such as an aryl group) in an organic solvent in the presence of a base. As a result of the reaction, the hydrogen in the amine compound can be substituted with —PR"R'" to produce the ligand compound of Chemical Formula 1 described above. In such a preparation method, the base or the organic solvent can be used without any particular limitation as long as they are the base or organic solvent which are known to be generally available in the substitution reaction of the amine compound and thus, the additional description thereof will be omitted.

The catalyst system for olefin oligomerization according to the present invention may comprise the ligand compound represented by Chemical Formula 1; a transition metal source; and a cocatalyst.

As used herein, the term "olefin oligomerization" means that a small number of olefins are polymerized to form an oligomer. When three olefins are polymerized, it is referred to as trimerization. When four olefins are polymerized, it is referred to as tetramerization, and the process of polymerization of a small number of olefins to form low molecular weight materials is collectively referred to as multimerization. Particularly, in the present invention, it refers to selectively preparing 1-hexene and 1-octene, main comonomers of LLDPE, from ethylene.

Further, the term "catalyst system" is independent of whether it is in a state of composition where the ligand compound, the transition metal source and the cocatalyst are simply mixed or whether they are reacted to form separate catalytic active species, and it may collectively refer to including these or the reaction products thereof as the catalytic active species as well as to any composition, compound and complex exhibiting a catalytic activity for the 'olefin oligomerization'.

The selective olefin oligomerization is closely related to a catalyst system used. A catalyst system used for olefin oligomerization comprises a transition metal source functioning as a main catalyst, and a cocatalyst, wherein the structure of the active catalyst may be changed according to the chemical structure of the ligand, thereby varying olefin selectivity and activity.

Thus, the catalyst system for olefin oligomerization according to the present invention can use a compound represented by Chemical Formula 1 as a ligand to consistently exhibit excellent multimerization activity during oligomerization of ethylene. Without being bound by any theory, it is predicted that the excellent activity of the catalyst system for oligomerization is expressed due to —NR$_1$R$_2$ (especially, certain types of R$_1$, R$_2$) or heterocyclic functional group that is bonded to the position of X. On the other hand, when the structure of the functional group bonded to the position of X is a little different (for example, when R$_1$ and R$_2$ are hydrogen or a C$_1$-C$_3$ alkyl group such as a methyl group, etc.), it was confirmed that the aforementioned superior activity cannot be expressed.

The transition metal source functions as a main catalyst, and for example, it may be a chromium source (chromium itself or chromium precursor), more specifically, one or more chromium precursors selected from the group consisting of chromium(III)acetylacetonate, tris(tetrahydrofuran) chromium trichloride, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate, and chromium(III)acetate hydroxide.

The cocatalyst is an organic metal compound including a Group 13 metal, and is not particularly limited as long as it can be used for olefin multimerization in the presence of a transition metal catalyst. Specifically, one or more cocatalysts selected from the group consisting of the compounds represented by the following Chemical Formulae 2 to 4 may be used.

—[Al(R$_7$)—O]$c$-    [Chemical Formula 2]

in Chemical Formula 2,
each of R$_7$ is independently a halogen, a C$_1$-C$_{20}$ alkyl group or a C$_1$-C$_{20}$ haloalkyl, and
c is an integer of 2 or more.

D(R$_8$)$_3$    [Chemical Formula 3]

in Chemical Formula 3,
D is aluminum or boron, and
$R_8$ is hydrogen, halogen, a $C_1$-$C_{20}$ alkyl or a $C_1$-$C_{20}$ haloalkyl.

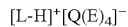 

in Chemical Formula 4,
L is a neutral Lewis base,
$[L-H]^+$ is a Bronsted acid,
Q is $Br^{3+}$ or $Al^{3+}$, and
each of E is independently a $C_6$-$C_{20}$ aryl or a $C_1$-$C_{20}$ alkyl, wherein the $C_6$-$C_{20}$ aryl or a $C_1$-$C_{20}$ alkyl is unsubstituted or substituted with one or more substituents selected from the group consisting of a halogen, a $C_1$-$C_{20}$ alkyl, a $C_1$-$C_{20}$ alkoxy, and a phenoxy.

Examples of the compound represented by Chemical Formula 2 may include a modified or unmodified $C_1$-$C_5$ alkyl aluminoxane, for example, methylaluminoxane (MAO), modified methylaluminoxane, ethylaluminoxane, isobutylaluminoxane, or butylaluminoxane.

Examples of the compound represented by Chemical Formula 3 may include trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tollylaluminum, dimethylaluminummethoxide, dimethylaluminumethoxide, trimethylboron, triethylboron, triisobutylboron, tripropylboron or tributylboron.

Examples of the compound represented by Chemical Formula 4 may include triethylammonium tetraphenylboron, tributylammonium tetraphenylboron, trimethylammonium tetraphenylboron, tripropylammonium tetraphenylboron, trimethylammonium tetra(p-tolyl)boron, tripropylammonium tetra(p-tollyl)boron, triethylammonium tetra(o,p-dimethylphenyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tollyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylboron, triphenylcarbonium tetraphenylaluminum, triphenylcarbonium tetra(p-trifluoromethylphenyl)boron, or triphenylcarbonium tetrapentafluorophenylboron.

The catalyst system for olefin oligomerization according to the present invention may have a mole ratio of the compound represented by Chemical Formula 1: the transition metal source: the cocatalyst of about 0.1:1:1 to about 10:1:10,000, preferably about 1:1:100 to about 5:1:3,000, so as to increase selectivity to linear alpha-olefin and multimerization activity. However, the present invention is not limited thereto.

In the catalyst system for olefin oligomerization comprising the ligand compound represented by Chemical Formula 1, the transition metal source, and the cocatalyst, the three components may be added simultaneously or sequentially in a random order in a suitable solvent in the presence or absence of monomers, and be obtained as an active catalyst. The suitable solvent may include heptane, toluene, cyclohexane, methylcyclohexane, 1-hexene, diethylether, tetrahydrofuran, acetonitrile, dichloromethane, chloroform, chlorobenzene, methanol, acetone, and the like, but is not limited thereto.

The present invention also provides a method for preparing olefin oligomer, comprising the step of multimerizing olefins in the presence of the catalyst system for olefin oligomerization. If the catalyst system for olefin oligomerization according to the present invention is used, a method for olefin oligomerization with improved activity may be provided. The olefin may preferably be ethylene.

The olefin oligomerization according to the present invention may be conducted as a homogeneous liquid phase reaction, a slurry reaction wherein a catalyst system is not dissolved in part or in whole, a two-phase liquid/liquid reaction, or a bulk phase reaction or a gas phase reaction wherein a product olefin acts as a main medium, in the presence or absence of an inert solvent, using the catalyst system for olefin oligomerization and a conventional device and contact technology, and the homogeneous liquid phase reaction is preferable.

The olefin oligomerization may be conducted in any inert solvent that does not react with a catalyst compound and an activator. The suitable inert solvent may include benzene, toluene, xylene, cumene, heptane, cyclohexane, methylcyclohexane, methylcyclopentane, hexane, pentane, butane, isobutane, and the like, but is not limited thereto. Herein, the solvent may be treated with a small amount of alkylaluminum to remove a small amount of water or air acting as a catalyst poison, before use.

The olefin oligomerization may be conducted at a temperature of about 5° C. to about 200° C. preferably about 30° C. to about 150° C. Further, the olefin oligomerization may be conducted under a pressure of about 1 bar to about 300 bar, preferably about 2 bar to about 150 bar.

According to examples of the invention, it was confirmed that as a result of oligomerizing ethylene with a catalyst system using the compound represented by Chemical Formula 1 as a ligand, it is possible to consistently exhibit higher activity when conducting oligomerization of olefins.

Hereinafter, the present invention will be described in detail with reference to the following examples. However, these examples are only to illustrate the invention, and the scope of the invention is not limited thereto.

In the following, all the reactions were conducted using Schlenk technique or a Glove box under argon atmosphere. The synthesized compounds were analyzed by $^1$H (500 MHz) and $^{31}$P (202 MHz) NMR spectra using a Varian 500 MHz spectrometer. Shift was expressed in ppm, downfield from TMS, with a residual solvent peak as a reference. A phosphorous probe was calibrated with aqueous $H_3PO_4$.

Synthesis Examples 1 to 5 and Comparative Synthesis Example 1: Preparation of the Ligand Compound First, phosphorus probe was titrated with an aqueous solution of phosphoric acid. The starting amine material (10 mmol) summarized in Table 1 below, and triethylamine (3 to 10 molar equivalents based on the starting amine material) were dissolved in 80 mL of dichloromethane under an argon atmosphere. Chlorodiphenylphosphine (20 mmol) was slowly added to a flask in a state of immersion in a water bath, and stirred overnight. After vacuum was applied to remove the solvent, THF was added to the mixture, thoroughly stirred and filtered with an air-free glass filter to remove triethylammonium chloride salt. The solvent was removed from the filtrate to yield a final product.

The NMR data of the starting amine materials used to prepare respective ligand compounds in the Synthesis Examples 1 to 5 and Comparative Synthesis Example 1, and of the ligand compounds formed from respective Synthesis Examples, are summarized and shown in Table 1 below.

TABLE 1

| | Starting amine material | NMR data |
|---|---|---|
| Synthesis Example 1 | 4-(1-pyrrolidinyl)-1-butaneamine | 62.0(s) |
| Synthesis Example 2 | 3-(4-methyl-1-piperazinyl)-propylamine | 62.5(s) |
| Synthesis Example 3 | 1-(3-aminopropyl)imidazole | 63.1(s) |
| Synthesis Example 4 | 2-picolylamine | 62.5(s) |
| Synthesis Example 5 | N-(3-aminopropyl)cyclohexylamine | 46.4(s), 64.3(s) |
| Comparative Synthesis Example 1 | 2-aminopropane | 48.4(br s) |
| Comparative Synthesis Example 2 | N,N-diisopropylethylene diamine | 61.5(s) |

Comparative Synthesis Example 2: Preparation of the Ligand Compound

The ligand compound having a structure of the following PNP 5 was prepared in accordance with the method described in Synthesis Example 4 of Korean Patent Laid-Open Publication No. 2012-0138309. The NMR data of the starting amine materials used to prepare the ligand compound in the Comparative Synthesis Example 2, and of the final ligand compound formed therefrom, are summarized and shown in Table 1 above.

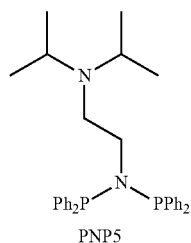

[PNP 5]

PNP5

Example 1: Ethylene Oligomerization

Under argon gas, Cr(acac)$_3$ (17.5 mg, 0.05 mmol) and the ligand compound prepared in the Synthesis Example 1 (0.1 mmol) were placed in a flask to which toluene (10 mL) was added, and the mixture was stirred to prepare a 5 mM solution.

A 100 mL Parr reactor was prepared, vacuum was applied for 2 hours, the internal atmosphere was then replaced with argon, and 46 mL of toluene and 2 mL of MAO (10 wt % toluene solution, Al/Cr=300) were added, and 2 mL of the 5 mM solution (10 µmol) was added into the reactor. The reactor was immersed in oil bath heated to 45° C. A valve of an ethylene line adjusted to 45 bar was opened to fill the inside of the reactor with ethylene, and the mixture was stirred at 600 rpm for 15 minutes. The ethylene line valve then was closed, the reactor was cooled to 0° C. with a dry ice/acetone bath, non-reacted ethylene was slowly vented, and 0.5 mL of nonane (GC internal standard) was added. After stirring for 10 seconds, 2 mL of the liquid part of the reactor was taken and quenched with water, and the organic part was filtered with a PTFE syringe filter to make a GC sample. The GC sample was analyzed with GC.

400 mL of ethanol/HCl (10 vol %) was added to the remaining reaction solution, and the mixture was stirred and filtered to obtain a polymer. The obtained polymer was dried overnight in a vacuum oven at 65° C., and the weight was measured.

Example 2: Ethylene Oligomerization

The oligomerization was conducted in the same manner as in Example 1, except that the ligand compound prepared in Synthesis Example 2 (0.1 mmol) was used instead of the ligand compound prepared in Synthesis Example 1 (0.1 mmol), and then the analysis was conducted.

Example 3: Ethylene Oligomerization

The oligomerization was conducted in the same manner as in Example 1, except that the ligand compound prepared in Synthesis Example 3 (0.1 mmol) was used instead of the ligand compound prepared in Synthesis Example 1 (0.1 mmol), and then the analysis was conducted.

Example 4: Ethylene Oligomerization

The oligomerization was conducted in the same manner as in Example 1, except that the ligand compound prepared in Synthesis Example 4 (0.1 mmol) was used instead of the ligand compound prepared in Synthesis Example 1 (0.1 mmol), and then the analysis was conducted.

Example 5: Ethylene Oligomerization

The oligomerization was conducted in the same manner as in Example 1, except that the ligand compound prepared in Synthesis Example 5 (0.1 mmol) was used instead of the ligand compound prepared in Synthesis Example 1 (0.1 mmol), and then the analysis was conducted.

Comparative Example 1: Ethylene Oligomerization

The oligomerization was conducted in the same manner as in Example 1, except that the ligand compound prepared in Comparative Synthesis Example 1 (0.1 mmol) was used instead of the ligand compound prepared in Synthesis Example 1 (0.1 mmol), and then the analysis was conducted.

Comparative Example 2: Ethylene Oligomerization

The oligomerization was conducted in the same manner as in Example 1, except that the ligand compound in Comparative Synthesis Example 2 (0.1 mmol) was used instead of the ligand compound prepared in Synthesis Example 1 (0.1 mmol), and then the analysis was conducted.

The results of Examples 1 to 5 and Comparative Examples 1 and 2 are shown in Table 2 below.

TABLE 2

| | Selectivity (wt %) | | | | Activity (kg/mol/Cr/hr) |
|---|---|---|---|---|---|
| | 1-hexene | 1-octene | 1-$C_{10}$ to 1-$C_{40}$ | Total | |
| Example 1 | 7.7 | 27.5 | 58.2 | 93.4 | 3673 |
| Example 2 | 10.8 | 40.5 | 38.4 | 89.7 | 3940 |
| Example 3 | 10.6 | 48.5 | 27.8 | 86.9 | 2332 |
| Example 4 | 8.9 | 25.5 | 55.7 | 90.1 | 2207 |
| Example 5 | 6.6 | 28.3 | 57.5 | 92.4 | 2838 |
| Comparative Example 1 | 17.2 | 63.4 | 13.8 | 94.4 | 1140 |
| Comparative Example 2 | 6.9 | 29.3 | 52.7 | 88.9 | 2182 |

As shown in Table 1, it was confirmed that the Examples using the compounds according to the present invention exhibited more excellent multimerization activity as compared with the Comparative Examples.

The invention claimed is:

1. A ligand compound represented by the following Chemical Formula 1:

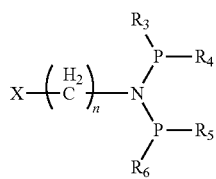

[Chemical Formula 1]

in Chemical Formula 1,

X is a pyrrolidinyl group substituted or unsubstituted with a $C_1$-$C_3$ alkyl group, or a piperazinyl group substituted or unsubstituted with a $C_1$-$C_3$ alkyl group, $R_3$ to $R_6$ are each independently a phenyl group, and n is an integer of 3 or 4.

2. The ligand compound according to claim 1 wherein the ligand compound is selected from the group consisting of the following compounds:

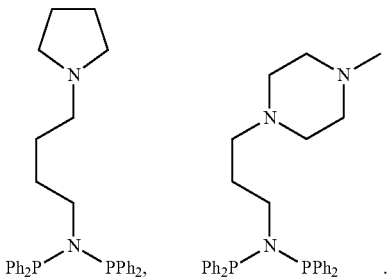

3. A catalyst system for olefin oligomerization comprising the ligand compound according to any one of claim 1; a transition metal source; and a cocatalyst.

4. The catalyst system for olefin oligomerization according to claim 3 wherein the transition metal source is a chromium source.

5. The catalyst system for olefin oligomerization according to claim 3 wherein the transition metal source is selected from the group consisting of chromium(III)acetylacetonate, tris(tetrahydrofuran)chromium trichloride, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate, and chromium (III)acetate hydroxide.

6. The catalyst system for olefin oligomerization according to claim 3 wherein the cocatalyst is selected from the group consisting of the compounds represented by the following Chemical Formulae 2 to 4, —[Al($R_7$)—O]$c$-     [Chemical Formula 2]

in Chemical Formula 2, each of $R_7$ is independently a halogen, a $C_1$-$C_{20}$ alkyl group or a $C_1$-$C_{20}$ haloalkyl, and c is an integer of 2 or more, D($R_8$)$_3$     [Chemical Formula 3]

in Chemical Formula 3,

D is aluminum or boron, and $R_8$ is hydrogen, halogen, a $C_1$-$C_{20}$ alkyl or a $C_1$-$C_{20}$ haloalkyl,

[L-H]$^+$[Q(E)$_4$]$^-$     [Chemical Formula 4]

in Chemical Formula 4,

L is a neutral Lewis base,

[L-H]$^+$ is a Bronsted acid,

Q is $Br^{3+}$ or $Al^{3+}$, and each of E is independently a $C_6$-$C_{20}$ aryl or a $C_1$-$C_{20}$ alkyl, wherein the $C_6$-$C_{20}$ aryl or $C_1$-$C_{20}$ alkyl is unsubstituted or substituted with one or more substituents selected from the group consisting of a halogen, a $C_1$-$C_{20}$ alkyl, a $C_1$-$C_{20}$ alkoxy, and a phenoxy.

7. The catalyst system for olefin oligomerization according to claim 3 for use in oligomerization of ethylene.

8. A method for olefin oligomerization comprising: the step of multimerizing olefins in the presence of the catalyst system for olefin oligomerization according to claim 3.

9. The method for olefin oligomerization according to claim 8 wherein the multimerization step is conducted at a temperature of 5° C. to 200° C.

10. The method for olefin oligomerization according to claim 8 wherein the multimerization step is conducted under a pressure of 1 bar to 300 bar.

11. The method for olefin oligomerization according to claim 8 wherein the olefin is ethylene.

12. A catalyst system for olefin oligomerization comprising the ligand compound according to claim 1; a transition metal source; and a catalyst.

13. A catalyst system for olefin oligomerization comprising the ligand compound according to claim 2; a transition metal source; and a catalyst.

* * * * *